United States Patent

Hashiguchi et al.

Patent Number: 5,856,347
Date of Patent: Jan. 5, 1999

[54] ANTIBACTERIAL PREPARATION OR BACTERICIDE COMPRISING 2-AMINOTHIAZOLE DERIVATIVE AND/OR SALT THEREOF

[75] Inventors: Terushi Hashiguchi; Toshio Yoshida, both of Tosu; Toshio Itoyama, Tsukuba; Yasuaki Taniguchi, Tosu, all of Japan

[73] Assignee: Hisamitsu Pharmaceutical Co., Inc., Tosu, Japan

[21] Appl. No.: 836,924

[22] PCT Filed: Nov. 16, 1995

[86] PCT No.: PCT/JP95/02347

§ 371 Date: May 23, 1997

§ 102(e) Date: May 23, 1997

[87] PCT Pub. No.: WO96/16650

PCT Pub. Date: Jun. 6, 1996

[30] Foreign Application Priority Data

Nov. 29, 1994 [JP] Japan .................................. 6-317737
Dec. 22, 1994 [JP] Japan .................................. 6-335388

[51] Int. Cl.$^6$ ................................. A61K 31/425
[52] U.S. Cl. ................................................ 514/390
[58] Field of Search ............................... 514/370

[56] References Cited

U.S. PATENT DOCUMENTS 5,449,783 9/1995 Saita et al. ............................... 514/370

Primary Examiner—Jerome D. Goldberg
Attorney, Agent, or Firm—Kubovcik & Kubovcik

[57] ABSTRACT

An antibacterial agent or bactericide, comprising a 2-aminothiazole derivative represented by the following formula (I) and a salt thereof:

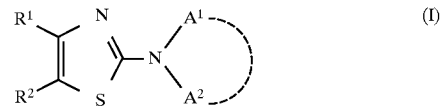

wherein $R^1$ and $R^2$ each represent a hydrogen atom; a halogen atom; a lower alkyl, lower cycloalkyl, substituted or unsubstituted phenyl, thiophene, benzoyl, benzoylmethyl, benzyl or substituted benzyl or p-pivaloyloxyphenyl group; —COOR wherein $R_3$ is a hydrogen atom, a lower alkyl group; and —$CH_2COOR_4$ wherein $R_4$ is a hydrogen atom or a lower alkyl, benzyl or substituted benzyl group; and $A^1$ and $A^2$ each represent a hydrogen atom; a lower alkanesulfonyl, halo lower alkanesulfonyl, phenyl or substituted phenyl, substituted benzoyl, substituted benzyl, substituted or unsubstituted benzenesulfonyl, substituted or unsubstituted lower alkanoyl or amidino group; —CO—$R_5$ wherein $R_5$ is a lower alkyl, phenyl or substituted phenyl group, —$(CH_2)_m$—COOH wherein m is an integer of 1 to 5, or —$(CH_2)_n$—NH—$R_6$ wherein n is an integer of 1 to 5 and $R_6$ is a hydrogen atom or a tert-butoxycarbonyl, benzyloxycarbonyl group; and —$(CH_2)_Q$—$R_7$ wherein Q is an integer of 0 to 5 and $R_7$ is a lower alkoxy, phenyl or substituted phenyl, pyridyl or substituted pyridyl, cyclic amino group; or $A^1$ and $A^2$ may combine with each other to form a cyclic amino group.

10 Claims, 1 Drawing Sheet

ANTIBACTERIAL PREPARATION OR BACTERICIDE COMPRISING 2-AMINOTHIAZOLE DERIVATIVE AND/OR SALT THEREOF

TECHNICAL FIELD

This invention relates to an antibacterial preparation or a bactericide, comprising a 2-aminothiazole derivative and/or a salt thereof. The term "bactericide" used herein connotes disinfectants.

BACKGROUND ART

Prior art will be described. At the outset, thiazoles having a trifluoromethanesulfonylamino group at the 2-position are described in U.S. Pat. Nos. 3,923,810 and 3,923,811. Japanese Pat. Appln. Laid-Open Gazettes Nos. Sho 64-40474 (40474/89) and Sho 64-75475 (75475/89) describe thiazole derivatives having anti-inflammatory action and analgesic action. Phenyl pivalate derivatives are described as an elastase inhibitor in U.S. Pat. No. 4,801,610 and Japanese Pat. Appln. Laid-Open Gazette No. Hei 3-20253 (20253/91). Further, the compounds or part of the compounds of this invention are described also in Japanese Pat. Appln. Laid-Open Gazettes Nos. Hei 3-173876 (173876/91) and Hei 5-70446 (70446/93). However, the antibacterial action or bactericidal action of the compounds of this invention is not disclosed at all, nor is it suggested.

DISCLOSURE OF THE INVENTION

An object of this invention is to provide an antibacterial preparation or a bactericide each of which comprises a comprising a 2-aminothiazole derivative and/or a salt thereof, exhibits a tendency of low bacterial tolerance thereto and low toxicity and has antibacterial activity or bactericidal activity, and the object is also to provide a pharmaceutical comprising the antibacterial preparation or the bactericide.

This invention relates to a novel antibacterial agent or bactericide comprising 2-aminothiazole derivatives and/or salts thereof as effective ingredients.

More specifically, this invention relates to 2-aminothiazole derivatives represented by the following general formula (1) and their salts useful as pharmaceutical preparations:

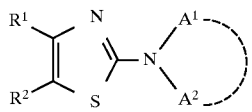 (I)

wherein
$R^1$ represents a lower alkyl group except when $R^2$ is a hydrogen atom; a substituted or unsubstituted phenyl group except 2,6-disubstituted phenyl group; a thiophene, benzoyl, benzoylmethyl or p-pivaloyloxyphenyl group; or —$CH_2COOR_4$ wherein $R_4$ is a hydrogen atom, or a lower alkyl or substituted or unsubstituted benzyl group;

$R^2$ represents a hydrogen atom; a halogen atom; a lower alkyl, lower cycloalkyl, substituted or unsubstituted phenyl, benzoyl, substituted or unsubstituted benzyl or p-pivaloyloxyphenyl group; —$COOR_3$ wherein $R_3$ is a hydrogen atom or a lower alkyl group; or —$CH_2COOR_4$ wherein
$R_4$ is a hydrogen atom, or a lower alkyl or substituted or unsubstituted benzyl group; and $A^1$ and $A^2$ may be identical with or different from each other and each represent a hydrogen atom; a lower alkanesulfonyl, halo lower alkanesulfonyl, or substituted or unsubstituted phenyl group except p-chlorophenyl group; a substituted benzyl, substituted or unsubstituted benzenesulfonyl, substituted or unsubstituted lower alkanoyl or amidino group; —CO—$R_5$ wherein $R_5$ is a lower alkyl, substituted or unsubstituted phenyl group, —$(CH_2)_m$—COOH wherein m is an integer of 1 to 5, or —$(CH_2)_n$—NH—$R_6$ wherein n is an integer of 1 to 5 and $R_6$ is a hydrogen atom or a tert-butoxycarbonyl or benzyloxycarbonyl group; or —$(CH_2)_Q$—$R_7$ wherein Q is an integer of 0 to 5 and $R_7$ is a lower alkoxy, substituted or unsubstituted phenyl, substituted or unsubstituted pyridyl or cyclic amino group; or $A^1$ and $A^2$ may combine with each other and the nitrogen atom to form a cyclic amino group.

The general formula (I) will be described in detail. The halogen atoms for $R^2$ include Fluorine, chlorine, bromine and iodine. The lower alkyl groups for $R^1$, $R_4$, $R^2$, $R_3$ and $R_5$ include $C_1$–$C_8$ alkyl groups such as methyl, ethyl, n-propyl, iso-propyl, n-butyl, iso-butyl and tert-butyl groups. When $R^2$ is a hydrogen atom, however, $R^1$ will not be a lower alkyl group. The lower cycloalkyl groups for $R^2$ include $C_3$–$C_6$ cycloalkyl groups such as cyclopropyl, cyclobutyl, cyclopentyl and cyclohexyl groups. The lower alkoxy groups for $R_7$ include $C_1$–$C_6$ alkoxy groups such as methoxy, ethoxy, n-propoxy, iso-propoxy, n-butoxy, iso-butoxy and tert-butoxy groups. The lower alkanesulfonyl groups for $A^1$ and $A^2$ include $C_1$–$C_4$ alkanesulfonyl groups such as methanesulfonyl, ethanesulfonyl, n-propanesulfonyl, iso-propanesulfonyl n-butanesulfonyl groups, iso-butanesulfonyl and tert-butanesulfonyl groups. The halo lower alkanesulfonyl group for $A^1$ and $A^2$ is a halo lower alkanesulfonyl group substituted by one or a plurality of halogen atoms, and the substituted alkanesulfonyl groups include mono-, di- or tri-fluoromethanesulfonyl, chloromethanesulfonyl, bromomethanesulfonyl, fluoroethanesulfonyl, chloroethanesulfonyl and bromoethanesulfonyl groups. The substituted lower alkanoyl group for $A^1$ and $A^2$ is a $C_1$–$C_4$ lower alkanoyl group substituted by an amino group or one to three halogen atoms, and the alkanoyl groups so substituted or not include aminoacetyl, monofluoroacetyl, difluoroacetyl, trifluoroacetyl, monochloroacetyl, dichloroacetyl, trichloroacetyl, monofluoropropionyl, difluoro-propionyl and trifluoropropionyl groups. The lower alkanoyl groups for $A^1$ and $A^2$ include $C_1$–$C_6$ alkanoyl groups such as acetyl, propionyl, butyryl, valeryl and pivaloyl groups. The cyclic amino groups composed of $A^1$, $A^2$ and a nitrogen atom include 5- or 6-membered cyclic amino groups containing a nitrogen atom and optionally containing an oxygen atom, such as piperidino, pyrrolidino, morpholino, piperazino and pipecolino groups (the cyclic amino groups may be further substituted by a halogen atom, a lower alkyl group or the like). The substituted phenyl groups for $R^1$, $R^2$, $A^1$, $A^2$, $R_5$ and $R_7$, substituted benzyl groups for $R^2$, $R_4$, $A^1$ and $A^2$, substituted pyridyl groups for $R_7$ and substituted benzenesulfonyl groups for $A^1$ and $A^2$ refer to those having the following substituents at their optional one to three positions. The substituents include lower alkyl groups, halogen atoms, hydroxyl groups, nitro groups, phenyl groups, trifluoromethyl groups, lower alkoxy groups, halo lower alkoxy groups substituted by one or a plurality of halogen atoms, lower alkanesulfonyl groups, halo lower alkanesulfonyl groups, amino groups; $C_1$–$C_6$ di-lower-alkylamino groups such as dimethylamino, diethylamino, di-n-propylamino and di-n-butylamino groups; $C_1$–$C_6$ lower alkylsulphenyl groups such as methylsulphenyl, ethylsulphenyl, n-propylsulphenyl, iso-propylsulphenyl, n-butylsulphenyl and tert-butylsulphenyl groups; $C_2$–$C_6$ lower alkanoylamino groups such as acetylamino, propionylamino, butyrylamino, iso-butyrylamino, valerylamino and pivaloylamino groups; lower alkanoyloxy groups; $C_1$–$C_4$ lower mercapto groups such as methylthio, ethylthio, n-propylthtio, iso-propylthio, n-butylthio, iso-butylthio and tert-butyl thio groups; acetic groups; $C_1$–$C_4$ acetic ester groups such as methyl acetate, ethyl acetate, propyl acetate and butyl acetate groups; $C_1$–$C_4$ glycolic ester groups such as methyl glycolate, ethyl glycolate, propyl glycolate and butyl glycolate groups; —(COOR$_4$ and —CH$_2$COOR$_4$ wherein R$_4$ is as defined above. However, the substituted phenyl groups for R$^1$ do not include 2,6-disubstituted phenyl groups. The substituted phenyl groups for A$^1$ and A$^2$ do not include p-chlorophenyl groups.

Pharmaceutically acceptable salts of the compounds represented by the general formula (I) include, but are not limited to, the salts of inorganic acids such as hydrochloric acid, sulfuric acid, nitric acid and phosphoric acid; the salts of organic acids such as maleic acid, fumaric acid, oxalic acid, succinic acid, malonic acid, lactic acid, citric acid, methanesulfonic acid, benzenesulfonic acid and acetic acid; inorganic salts, for example, alkali metal salts such as lithium salts, sodium salts and potassium salts, alkaline earth metal salts such as calcium salts and magnesium salts, and ammonium salts; and organic salts such as triethylamine salts, ethanolamine salts, triethanolamine salts and dicyclohexylamine salts.

When the compound represented by the general formula (I) or a salt thereof is used as a medicine, it may be used in the form of general medicinal preparation, such as injections, external preparations for local applications, and oral preparations. The preparation may be formed by using conventional diluents or excipients, such as fillers, extenders, binders, humectants, disintegrators, surfactants and lubricants.

Typical forms of the preparations include tablets, pills, suppositories, injections, pastes, ointments, creams, gels, gel-like creams, lotions, poultices, plasters, liniments, liquid preparations, aerosols, powders, granules, capsules, syrups, stomatic preparations, eye drops and nasal drops. The preparation in a suitable form may be stably administered systemically or locally and orally or parenterally.

Carriers commonly used in the art may be used in tabletting the preparations, and they include excipients, such as lactose, saccharose, sodium chloride, glucose, urea, starch, calcium carbonate, kaolin, crystalline cellulose, and silicic acid; binders, such as water, ethanol, propanol, simple syrup, glucose solution, starch solution, gelatin solution, carboxymethyl cellulose, shellac, methyl cellulose, potassium phosphate, and polyvinyl pyrrolidone; disintegrators, such as dry starch, sodium alginate, agar powder, laminaran powder, sodium hydrogencarbonate, calcium carbonate, polyoxyethylene sorbitan fatty acid esters, sodium laurylsulfate, monoglyceride stearate, starch, and lactose; disintegration inhibitors, such as saccharose, stearin, cacao butter, and hydrogenated oil; absorption promoters, such as quaternary ammonium base and sodium laurylsulfate; humectants, such as glycerin and starch; adsorbents, such as starch, lactose, kaolin, bentonite, and colloidal silicic acid; and lubricants, such as purified talc, salts of stearic acid, boric acid powder, and polyethylene glycol. The tablet may be, if necessary, a tablet having a usual coating, for example, sugar coated tablet, gelatin coated tablet, enteric coated tablet, film coated tablet, double layer tablet, or multilayer tablet.

In the preparation of pills, carriers commonly used in the art may be applied, and examples thereof include excipients, such as glucose, lactose, starch, cacao butter, hydrogenated vegetable oil, kaolin, and talc; binders, such as powdered acacia, powdered tragacanth, gelatin, and ethanol; and disintegrators, such as laminaran agar.

In the preparation of suppositories, bases for suppositories may be suitably selected from those commonly used in the art, that is, from lipophilic, water-soluble and emulsion bases. The base for a suppository may be selected from synthetic oleaginous bases, such as cacao butter, hydrogenated peanut oil, and hydrogenated coconut oil, and water-soluble bases, such as polyethylene glycols, Monolene, Twolene, and Pluronic, and 0.01 to 10% by weight of an antibacterial preparation or a bactericide as an medicinal ingredient. The base may be incorporated with 0.01 to 5% by weight of an ultraviolet absorber, and, if necessary, 0.01 to 5% by weight of an antioxidant to prepare a suppository preparation containing the antibacterial preparation or bactericide according to this invention.

A local analgesic, an antihistamic, a local astringent, a sulfonamide, an antibiotic, a wound treating agent, a surfactant, a vitamin, a crude drug extract, a bile acid, a preservative, an excipient, an absorption promotor, an amino acid and the like may be used as optional additives.

In the case of an injection, a liquid preparation, an emulsion, and a suspension are sterilized and are preferably isotonic to blood. In the preparation of the liquid, emulsion, and suspension preparations, a wide variety of diluents commonly used in the art may be applied, and examples thereof include water, an aqueous lactic solution, ethyl alcohol, propylene glycol, and a polyoxyethylene sorbitan fatty acid ester. In this case, salt, glucose or glycerin in an amount sufficient to prepare an isotonic solution may be incorporated into the pharmaceutical, and, in addition, conventional solubilizing agents, buffers, and soothing agents may be added. Further, if necessary, colorants, preservatives, perfumes, flavours, sweetening agents, and other pharmaceuticals may be incorporated into the pharmaceutical.

Ointments, gels, creams, lotions, and pastes will be described.

The ointments according to this invention will be explained first compounds for the base for the ointments are selected from known or conventionally-used ones and preferably selected form the group of higher fatty acids and esters thereof (such as adipic acid, myristic acid, palmitic acid, stearic acid, oleic acid, adipic acid ester, myristic acid ester, palmitic acid ester, diethyl sebacate, hexyl laurate and cetyl isooctanate), waxes (such as spermaceti, beeswax and ceresine), surface active agents (such as polyoxyethylene alkyl ether phosphoric esters), higher alcohols (such as cetanol, stearyl alcohol and cetostearyl alcohol), silicone oils (such as dimethylpolysiloxane, methylphenylpolysiloxane, glycolmethylpolysiloxane and silicon glycol copolymer), hydrocarbons (such as hydrophilic vaseline, white vaseline, purified lanolin and liquid paraffin), water, absorbefacients (such as propylene carbonate, diisopropyl adipate, crotamiton, azone and pirotiodecane), humectants (such as glycerin, propylene glycol, butylene glycol and sorbitol), rash-preventing agents and other additives. Some of the above compounds selected for the base are mixed with the antibacterial preparation or bactericide, which is a medicinal ingredient, to obtain an ointment of this invention.

One example of the preparation of ointments will be described.

0.01 to 10% by weight of an antibacterial preparation or a bactericide is mixed with 5 to 15% by weight of a higher fatty acid ester and 1 to 10% by weight of a surfactant at room temperature or under heating. The mixture so obtained is incorporated with 4 to 10% by weight of a wax and 50 to 90% by weight of a hydrocarbon, then heated or heat-melted and kept at 50° to 100° C. After all the ingredients are dissolved to constitute a transparent solution, the solution is homogeneously mixed by means of a homomixer, followed by lowering the solution to room temperature while stirring to prepare the ointment of this invention. It is needless to say that the above preparation example is only an example and the ointment may be prepared by conventional methods and formulations or methods and formulations similar thereto. The order of addition of each ingredient is also not particularly limited. This is true of the following formulation examples and preparation examples.

The gels according to this invention will be explained. Compounds for the base for the gels are selected from known or conventionally-used various bases. Such a base may include lower alcohols (such as ethanol and isopropyl alcohol), water, gelatinizers (such as carboxyvinyl polymer, hydroxyethyl cellulose, hydroxypropyl cellulose, methyl cellulose, ethyl cellulose, carboxymethyl cellulose and alginic acid propylene glycol ester), neutralizing agents (such as triethanolamine, diisopropanolamine and sodium hydroxide), surface active agents (such as sorbitan sesquioleate, sorbitan trioleate, sorbitan monooleate, sorbitan monostearate, sorbitan monolaurate, polyethylene glycol monostearate, polyoxyethylene nonylphenyl ether, polyoxyethylene cetyl ether and polyoxyethylene lauryl ether), absorbefacients (such as propylene carbonate, diethyl sebacate, diisopropyl adipate, crotamiton, azone, propylene glycol and pirotiodecane), rash-preventing agents and other additives. Some of the above compounds selected for the base are mixed with the antibacterial preparation or bactericide, which is a medicinal ingredient, to obtain a gel of this invention.

One example of the preparation of the gel will be described.

(A) 0.5 to 5% by weight of a gelling agent is added to and swollen with not more than 55% by weight of water. (B) Separately, 0.01 to 10% by weight of an antibacterial preparation or a bactericide is dissolved or suspended in a solubilizing agent, the solution or suspension is dissolved in a mixture of not more than 40% by weight of a glycol with not more than 60% by weight of a lower alcohol. The component (B) is then added to the component (A), and incorporated with a neutralizing agent to adjust the whole to a pH of 4 to 7, thereby preparing the gel according to this invention.

The creams according to this invention will be explained. Compounds for the base for the creams are selected from known or conventionally-used various bases. Such bases are exemplified by esters of higher fatty acids (such as myristic acid ester, palmitic acid ester, diethyl sebacate, hexyl laurate and cetyl isooctanate), lower alcohols (such as ethanol and isopropanol), hydrocarbons (such as liquid paraffin and squalane), polyhydric alcohols (such as propylene glycol and 1,3-butylene glycol), higher alcohols (such as 2-hexyl decanol, cetanol and 2-octyldodecanol), emulsifiers (such as polyoxyethylene alkyl ethers, fatty acid esters and polyethylene glycol fatty acid esters), antiseptics (such as para-hydroxybenzoic acid ester), absorbefacients (such as propylene carbonate, diethyl sebacate, diisopropyl adipate, crotamiton, azone and pirotiodecane), rash-preventing agents and other additives. Some of the above compounds selected for the base are incorporated with the antibacterial preparation or bactericide, which is a medicinal ingredient, to obtain a cream of this invention.

Further, the gel-like creams of this invention having properties which are intermediate between those of cream and gel, can be obtained by mixing the cream mentioned above with a gelatinizer (such as carboxyvinyl polymer, hydroxyethyl cellulose, hydroxypropyl cellulose, ethyl cellulose or carboxymethyl cellulose) and a neutralizing agent (such as diisopropanolamine, triethanolamine or sodium hydroxide) and then adjusting the whole to a pH value of 4–8, preferably 5–6.5.

One example of the preparation of a gel-like cream will be described.

(A) 0.01 to 10% by weight of an antibacterial preparation or a bactericide is dissolved in a mixture of not more than 25% by weight of a higher fatty acid ester with not more than 40% by weight of a lower alcohol, and incorporated with not more than 0.5% by weight of an antiseptic and not more than 5% by weight of an emulsifier. Separately, (B) 0.5 to 5% by weight of a gelling agent is added to and swollen with water. The component (B) is then added to the component (A), the mixture is homogeneously emulsified by means of a homo-mixer. After the completion of the emulsification, the obtained emulsion is incorporated with a neutralizing agent to adjust the pH to 4 to 8, thereby preparing the gel-like cream of this invention.

The poultices according to this invention will be explained. Compounds for the base for the poultices are selected from adhesive agents (such as synthetic water-soluble polymers including sodium polyacrylate, polyacrylic acid, poval, polyvinyl pyrrolidone, polyethylene oxide and polyvinyl methacrylate; natural products including arabic rubber, starch and gelatin; and others including methyl cellulose, hydroxypropyl cellulose, alginic acid, sodium alginate, ammonium alginate and sodium carboxymethyl cellulose), moistening agents (such as urea, glycerin, propylene glycol, butylene glycol and sorbitol), fillers (such as kaolin, zinc oxide, talc, titanium, bentonite, epoxy resins, organic acids (citric acid, tartaric acid, maleic acid, maleic acid anhydride, succinic acid and the like), calcium, magnesium and aluminium), water, solubilizers (such as propylene carbonate, crotamiton and diisopropyl adipate), tackifiers (such as rosin, ester gum, polybutene and polyacrylic acid ester), rash-preventing agents (such as diphenhydramine hydrochloride, chlorpheniramine maleate, glycyrrhizic acid, dexamethasone, betamethasone and fluocinolone acetonide), and other additives (such as salicylic acid, methyl salicylate, glycol salicylate, l-menthol, (camphor, nonylic acid vanillylamido, thymol, red pepper extract, mentha oil, azone and pirotiodecane). Some of the above compounds selected for the base are incorporated with the antibacterial preparation or bactericide, which is a medicinal ingredient, to obtain a poultice of this invention.

One example of the preparation of the poultice will be described.

(A) 0.01 to 10% by weight of an antibacterial preparation or a bactericide is mixed and dissolved in 0.5 to 8% by weight of a solubilizer to prepare a homogeneous solution. Subsequently, (B) 5 to 20% by weight, preferably 10 to 15% by weight, of a thickening agent is mixed with and dispersed in 5 to 40% by weight of a wetting agent and 10 to 80% by weight of water, and incorporated with not more than 20% by weight of a filler to prepare a homogeneous kneaded product. The component (A) is then added to and mixed with the component (B) to prepare a homogeneous kneaded product. The kneaded product is spread and applied on a support by a conventional method, and a releasable covering material is applied thereon to prepare the poultice of this invention. The support may be suitably selected from the group consisting of stretchable or unstretchable cloth, nonwoven fabric, nonwoven paper and the like, and the releasable covering material may be suitably selected from the group consisting of polyethylene, polypropylene, polyvinyl chloride, a polyester, polyvinylidene chloride, silicone-treated paper and the like.

The plasters according to this invention will be explained. Compounds for the base for the plasters are selected from known polymers (such as acrylic compositions which are copolymers with vinyl monomers such as methacrylic acid esters, acrylonitrile, vinyl acetate and vinyl propionate;

silicone resin; polyisoprene rubber; polyisobutylene rubber; natural rubber; acrylic rubber; styrene-butadiene-styrene block copolymer; and styrene-isoprene-styrene block copolymer), fats and oils or higher fatty acids (such as almond oil, olive oil, tsubaki oil, persic oil, peanut oil, oleic acid, liquid paraffin and polybutene), tackifiers (such as rosin, rosin denatured maleic acid and hydrogenated rosin ester), and rash-preventing agents. Some of the above compounds selected for the base are incorporated with other additives (such as dl-camphor, l-menthol, thymol, nonylic acid vanillylamido, red pepper tincture, mentha oil, crotamiton, peppermint oil, azone and pirotiodecane) as required and then mixed with the antibacterial preparation or bactericide, which is a medicinal ingredient, to obtain a mixture. The thus obtained mixture is applied on an expansible or non-expansible carrier (such as polypropylene, polyester, poly vinylidene chloride, polyacryl, polyurethane, rayon, cotton, ethylene-vinyl acetate copolymer, fabric, nonwoven fabric or nonwoven paper), after which a coating material which will be peeled off when used is stuck on the mixture applied to obtain a plaster of this invention. The plaster may be prepared simply by a conventional method. Regarding the formulation, the medicinal ingredient of a conventional cold or hot plaster is replaced with 0.01 to 10% by weight of an antibacterial preparation or a bactericide, and 0.01 to 5% by weight of an ultraviolet absorber and, if necessary, 0.01 to 5% by weight of an antioxidant are incorporated therein to prepare the plaster of this invention.

The liniments according to this invention will be explained. The liniment can be obtained by incorporating 0.01–10 wt. % of the antibacterial preparation or bactericide, which is a medicinal ingredient, with 10–70 wt. % of an alcohol (such as a monohydric alcohol including ethanol, propanol or isopropanol or a polyhydric alcohol including polyethylene glycol, propylene glycol or butylene glycol), up to 55 wt. % of water, up to 60 wt. % of a fatty acid ester (such as an ester of adipic acid, sebacic acid or myristic acid) and up to 10 wt. % of a surface active agent (such as polyoxyethylene alkyl ether), and further mixing with 0.01–5 wt. % of an ultraviolet light absorber and 0.01–5 wt. % of an antioxidant as required thereby to obtain a liniment of this invention.

The above formulation example and preparation example are a mere example, and it is needless to say that the liniment of this invention can be prepared by a conventional method for preparing a liniment. Further, regarding the composition of the liniment, the liniment of this invention can be prepared simply by replacing the medicinal ingredient of a conventional liniment with an antibacterial preparation or a bactericide and incorporating an ultraviolet absorber into the liniment. The liniments of this invention may contain, as required, a neutralizing agent to be used for adjustment of pH, a viscosity-increasing agent such as methyl cellulose, carboxyvinyl polymer or hydroxypropyl cellulose, a rash-preventing agent and other additives (such as salicylic acid, methyl salicylate, glycol salicylate, l-menthol, camphor, mentha oil, red pepper extract, nonylic acid vanillylamido, thymol, crotamiton, azone, propylene carbonate, diisopropyl adipate and pirotiodecane).

The liquid preparation will now be described. The liquid preparation is used particularly as a disinfectant. The amount of the antibacterial preparation or bactericide in the liquid preparation is 0.01 to 10% by weight.

Preferred lower monoalcohols which may be used in the liquid preparation according to this invention are primary, secondary and tertiary monoalcohols having 1 to 4 carbon atoms, and examples thereof include ethanol, ethanol for disinfection, anhydrous ethanol, isopropanol, propanol, and butanol. The amount of the lower monoalcohol in the liquid preparation is preferably 60 to 90% by weight based on the whole liquid preparation. When the amount of the lower monoalcohol incorporated is less than 60% by weight, no satisfactory antibacterial action or bactericidal action will be attained. On the other hand, when it exceeds 90% by weight, the foam retention time will be short, rendering some of the resulting liquid preparations unsuitable for practical use.

Nonionic surfactants which may be incorporated into the liquid preparation of this invention include polyoxyethylene sorbitan acyl esters, such as Polysorbate 80, Polysorbate 60, and Polysorbate 20, and silicone/polyether copolymers, such as dimethylsiloxane/methyl (POE) siloxane copolymers; polyoxyethylene acyl esters, such as polyoxyl stearate 40 and polyoxyethylene lauryl ether; polyoxyethylene alcohol ethers, such as lauromacrogol; glycerin stearates, such as glycerin monostearate and decaglycerin monolaurate; sorbitan fatty acid esters, such as span 60 monostearate; sorbitan acyl esters, such as sorbitan sesquioleate; polyoxy hydrogenated castor oils, such as HCO-60 and HCO-50; polyoxyethylene propylene glycol monofatty acid esters, such as Pluronic F68. These nonionic surfactants may be used alone or in combination of two or more of them in a suitable proportion.

Preferably, the nonionic surfactant has an HLB of not less than 10. When the HLB is less than 10, it is often difficult to provide contemplated foam having suitable stability. The amount of the surfactant in the liquid preparation is preferably 0.5 to 3% by weight and more preferably 1 to 3% by weight, based on the whole liquid preparation. When the amount of the surfactant is less than 0.5% by weight or larger than 3% by weight, it is often difficult to provide foam having suitable stability as in the case of HLB.

The water-soluble polymer compound used may be either a naturally occurring or a synthetic polymer compound. The naturally occurring polymer compounds usable herein include soluble polysaccharides, such as acacia gum, xanthan gum, pectin, carageenan, and sodium alginate; soluble polypeptides, such as gelatin; and chitins, such as chitin and chitosan. On the other hand, the synthetic polymer compounds usable herein include polymers prepared by partial chemical modification of naturally occurring polymer compounds, for example, soluble polysaccharides, such as carboxymethyl cellulose sodium and hydroxypropyl cellulose. Pure synthetic polymers include polyvinyl alcohol compounds, such as polyvinyl alcohol and derivatives thereof, polyvinyl pyrrolidone compounds, such as polyvinyl pyrrolidone and derivatives thereof. Among them, xanthane gum is preferred from the viewpoint of foam stability. The amount of the polymer compound in the liquid preparation is preferably 0.01 to 3% by weight based on the whole liquid preparation. When it is outside the above amount range, as described above, it is often difficult to provide foam having suitable stability.

Humectants which may be incorporated into the liquid preparation according to this invention include glycerin, propylene glycol, sorbitol, 1,3-butylene glycol, macrogol 400, and hyaluronic acid. Glycerin is particularly preferred from the viewpoint of foam stability, antifoaming property, and moisture retention. These humectants may be used alone or in combination of two or more of them in any proportion. However, glycerin, propylene glycol, sorbitol, 1,3-butylene glycol, and macrogol 400 among the above humectants are preferably incorporated in an amount of 1 to 10% by weight based on the whole liquid preparation, while hyaluronic acid is preferably incorporated in an amount of 0.01 to 1% by weight based on the whole liquid preparation.

Further, water may be incorporated into the liquid preparation of this invention. In this case, the amount of water incorporated may be 3 to 35% by weight based on the whole liquid preparation. Water acts together with the surfactant to improve the foam forming property and acts together with a water-soluble polymer compound to stabilize the foam.

It has been known that alcohols useful as a liquid preparation, such as ethanol, when incorporated in a high concentration into a foam preparation, the foam generated will become unstable and disappear in the early stages. According to this invention, the use of a lower monoalcohol in a high concentration in combination with a predetermined nonionic surfactant permits the retention time of foam to be suitably adjusted. In general, when in use, about 0.5 to 2 g of a foamy liquid preparation is placed in the palm of the hand, followed by rubbing it with the hand, the foam retention time for which the liquid preparation is satisfactorily spread and offers such a feeling to users that the retention is not too long, is experientially 5 to 30 sec. In order to prepare a liquid preparation which is easy to handle and, at the same time, is effective, it is necessary to bring the foam retention time to the above range while using an alcohol in a high concentration. Further, the incorporation of a suitable amount of a water-soluble polymer compound into the liquid preparation of this invention permits the form of the foam to be distinctly and stably retained.

The liquid preparation of this invention may be generally used in combination with a propellant to prepare an aerosol composition. Propellants usable herein include those commonly used in aerosols, such as dimethyl ether, liquefied petroleum gas, $N_2$ gas, nitrous oxide gas, $CO_2$ gas, and alternative flon gas. Compressed air may be used instead of the above propellant. Alternatively, a mixture of these materials may also be used. The amount of the propellant incorporated is not particularly limited. It, however, is preferably 0.1 to 80% by weight based on the total amount of the liquid preparation.

Besides the above ingredients, if necessary, perfumes or ingredients commonly incorporated in preparations for external use, for example, l-menthol, tocopherol acetate, and fats and oils, for example, vegetable and animal oils, such as a castor oil and squalene, may be used in a suitable amount.

The dose of the antibacterial preparation or bactericide of this invention may be suitably determined depending upon symptom, age, sex and the like of persons to which the antibacterial preparation or bactericide is to be administered. In general, when the antibacterial preparation or bactericide is orally administered to an adult, the compound (I) or salt thereof is preferably administered at a dose of about 10 to 500 mg per time and once or several times per day.

The effective ingredient in this invention will be described. The compound represented by the general formula (I) may be prepared, for example, by a process described in Japanese Pat. Appln. Laid-Open Gazette No. Hei 3-173876 (173876/91) or a process similar thereto.

It may be prepared, for example, by processes represented by the following formulae.

Process 1

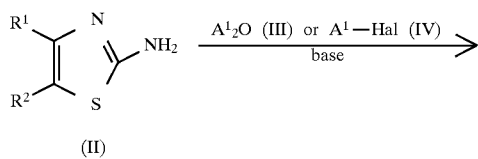

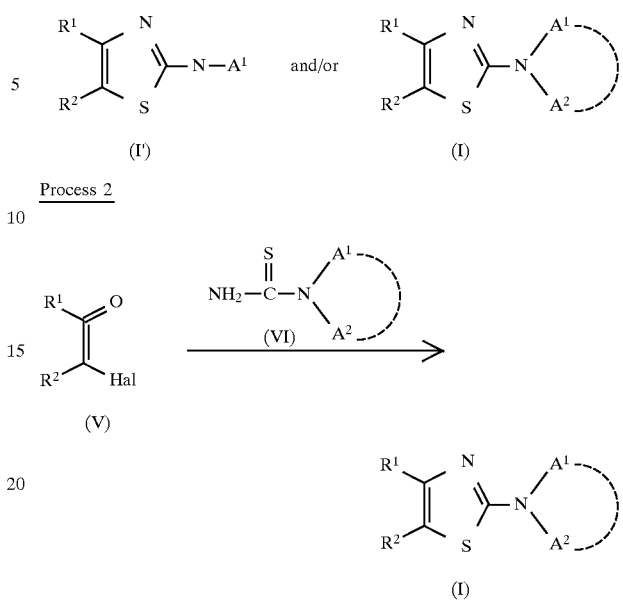

wherein $R^1$, $R^2$, $A^1$, and $A^2$ are as defined above and Hal represents a halogen atom.

According to the process 1, a compound represented by the general formula (II) may be reacted with a compound represented by the general formula (III) or (IV) in a suitable solvent in the presence of a base catalyst under cooling, room temperature, or heating for about 0.5 to 30 hr to prepare the compound represented by the general formula (I) or (I'). The solvent used in this reaction is not particularly limited so far as it is an organic solvent inert to the reaction, and examples thereof include dichloromethane, chloroform, carbon tetrachloride, tetrahydrofuran, N,N-dimethylformamide, N,N-dimethylacetamide, and dimethyl sulfoxide. Base catalysts usable herein include, but are not limited to, basic catalysts which accelerate deacidification, such as pyridine, collidine, triethylamine, and tri-n-butylamine.

According to the process 2, a compound represented by the general formula (V) may be mixed with a compound represented by the general formula (VI) in a suitable solvent at room temperature or with heating to give the compound represented by the general formula (I). Solvents usable in the reaction include, but are not limited to, methanol, ethanol, tetrahydrofuran, N,N-dimethylformamide, and dimethyl sulfoxide.

BRIEF DESCRIPTION OF THE DRAWINGS

In FIGS. 1 and 2, ● represents compound No. 9 system 1, ○ compound No. 9 system 2, ♦ GM system 1, and □ GM system 2.

BEST MODE FOR CARRYING OUT THE INVENTION

Figure 1:
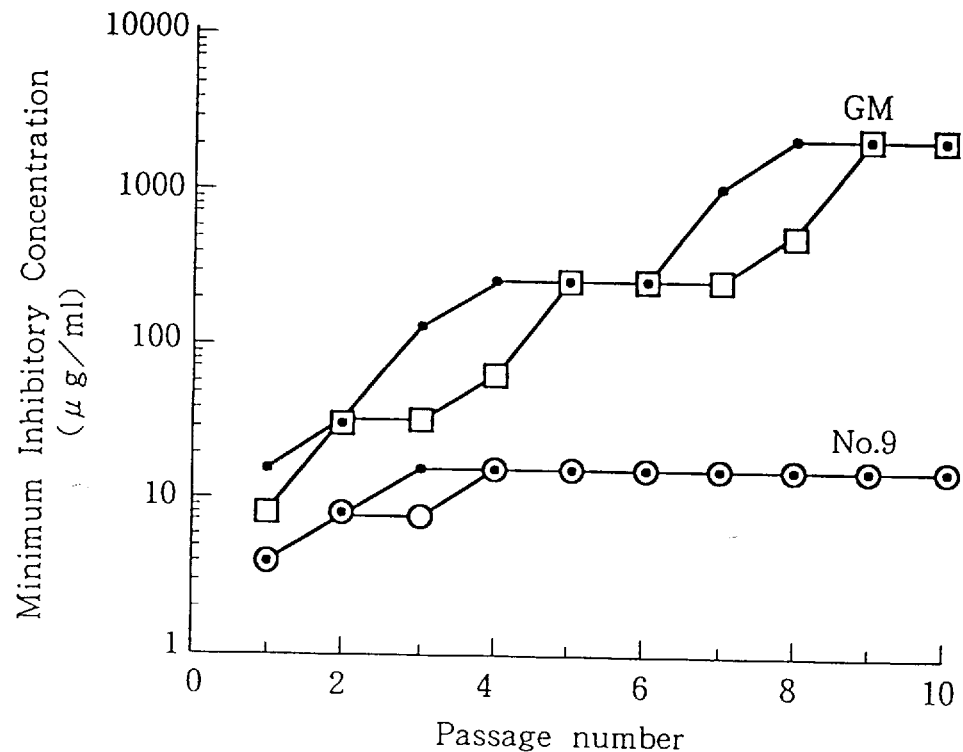
FIG. 1 is graphs showing the relationship between the Minimum Inhibitory Concentration (MIC) and the passage number for *Staphylococcus aureus.

Some of the compounds represented by the general formula (I) are specifically summarized in Table 1.

TABLE 1

![Structure: thiazole ring with R¹ at 4-position, R² at 5-position, N-C(=S) with N bearing A¹ and A²]

| Compound No. | R¹ | R² | A¹ | A² | Melting point (°C.) |
|---|---|---|---|---|---|
| 1 | phenyl | phenyl | SO₂CF₃ | H | 212–214 |
| 2 | 4-CH₃O-phenyl | 4-CH₃O-phenyl | SO₂CF₃ | H | 240–242 |
| 3 | 4-F-phenyl | 4-F-phenyl | SO₂CF₃ | H | 193–195 |
| 4 | phenyl | phenyl | SO₂CH₂Cl | H | 201–203 |
| 5 | 4-CH₃O-phenyl | 4-CH₃O-phenyl | SO₂CH₂CF₃ | H | 259–261 |
| 6 | phenyl | phenyl | 4-CF₃-C₆H₄-SO₂ | H | 248–249 |
| 7 | phenyl | 3,4-di-F-phenyl | SO₂CF₃ | H | 190.5–192 |

TABLE 1-continued

| Compound No. | R¹ | R² | A¹ | A² | Melting point (°C.) |
|---|---|---|---|---|---|
| 8 | 4-Cl-C₆H₄ | C₆H₅ | SO₂CF₃ | H | 223–225 |
| 9 | 4-CH₃O-C₆H₄ | C₆H₅ | SO₂CF₃ | H | 219–221 |
| 10 | 4-CH₃O-C₆H₄ | 4-Cl-C₆H₄ | SO₂CF₃ | H | 164–165 (dec.) |
| 11 | C₆H₅ | 4-Cl-C₆H₄ | SO₂CF₃ | H | 202–204 |
| 12 | 4-Cl-C₆H₄ | 4-Cl-C₆H₄ | SO₂CF₃ | H | 221–222 |
| 13 | 4-F-C₆H₄ | C₆H₅ | SO₂CF₃ | H | 176–178 |
| 14 | 4-F-C₆H₄ | 4-Cl-C₆H₄ | SO₂CF₃ | H | 165–167 |
| 15 | C₆H₅ | 4-Cl-C₆H₄ | SO₂CF₃ | H | 215–217 |

Structure heading: R¹, R² attached to C=C-S-C(=N-)—N(A¹)(A²) (thiazoline-type ring)

TABLE 1-continued
| Compound No. | R¹ | R² | A¹ | A² | Melting point (°C.) |
|---|---|---|---|---|---|
| 16 | phenyl | 4-NO$_2$-phenyl | SO$_2$CF$_3$ | H | 212.5–214 |
| 17 | phenyl | 4-NH$_2$-phenyl | SO$_2$CF$_3$ | H | 216–218 |
| 18 | 4-CH$_3$O-phenyl | 4-CH$_3$O-phenyl | SO$_2$CH$_3$ | H | 208–210 |
| 19 | 4-F-phenyl | 4-F-phenyl | SO$_2$CH$_3$ | H | 222–224 |
| 20 | phenyl | 4-NO$_2$-phenyl | SO$_2$CH$_3$ | H | 233–235 |
| 21 | 4-F-phenyl | 4-F-phenyl | SO$_2$CH$_3$ | SO$_2$CH$_3$ | 213–215 |
| 23 | phenyl | 4-NO$_2$-phenyl | SO$_2$CH$_3$ | SO$_2$CH$_3$ | 203–205 |
| 24 | 4-CH$_3$SO$_2$O-phenyl | phenyl | | SO$_2$CH$_3$ | 199–201 |

TABLE 1-continued

Structure:
$$R^1\text{-C(=N-)-C(R^2)=S} \text{ with N bearing } A^1 \text{ and } A^2$$

| Compound No. | R¹ | R² | A¹ | A² | Melting point (°C.) |
|---|---|---|---|---|---|
| 25 | phenyl | phenyl | SO₂CH₂CF₃ | H | 192–194 |
| 26 | 4-F-phenyl | 4-F-phenyl | SO₂CH₂CF₃ | H | 207–209 |
| 27 | phenyl | phenyl | 4-Cl-C₆H₄-SO₂ | H | 268–270 |
| 28 | 4-CH₃-phenyl | phenyl | SO₂CF₃ | H | 186.5–188.5 |
| 29 | phenyl | 4-CH₃-phenyl | SO₂CF₃ | H | 210.5–212 |
| 30 | 4-CH₃-phenyl | 4-CH₃-phenyl | SO₂CF₃ | H | 216.5–217 |
| 31 | phenyl | 4-CH₃O-phenyl | SO₂CF₃ | H | 188–190 |
| 32 | 4-NO₂-phenyl | phenyl | SO₂CF₃ | H | 228–230 |

TABLE 1-continued

| Compound No. | R¹ | R² | A¹ | A² | Melting point (°C.) |
|---|---|---|---|---|---|
| 33 | 4-CH₃O-C₆H₄ | 4-F-C₆H₄ | SO₂CF₃ | H | 222–224 |
| 34 | C₆H₅ | 2-F-C₆H₄ | SO₂CF₃ | H | 184–185 |
| 35 | C₆H₅ | 3-F-C₆H₄ | SO₂CF₃ | H | 214–217 |
| 36 | C₆H₅ | 4-F-C₆H₄ | SO₂CF₃ | H | 197–198.5 |
| 37 | 4-F-C₆H₄ | 3-F-C₆H₄ | SO₂CF₃ | H | 165–167 |
| 38 | C₆H₅ | 2,4-F₂-C₆H₃ | SO₂CF₃ | H | 176–177.5 |
| 39 | C₆H₅ | C₆H₅ | SO₂CF₃ | CH₂CH₃ | 124–125.5 |

TABLE 1-continued

Structure: R¹ and R² on C=C, with C bonded to S and N; N connected to A¹ and A² (ring).

| Compound No. | R¹ | R² | A¹ | A² | Melting point (°C.) |
|---|---|---|---|---|---|
| 40 | 4-CH₃S-C₆H₄ | C₆H₅ | SO₂CF₃ | H | 212–215 |
| 41 | C₆H₅ | C₆H₅ | SO₂CH₃ | H | 221–222 |
| 42 | C₆H₅ | C₆H₅ | 4-NH₂-C₆H₄-SO₂ | H | 194–196 |
| 43 | C₆H₅ | C₆H₅ | 4-NO₂-C₆H₄-SO₂ | H | 233–235 |
| 44 | C₆H₅ | C₆H₅ | COCF₃ | H | 240–242 |
| 45 | 4-F-C₆H₄ | 4-F-C₆H₄ | COCF₃ | H | 213–216 |
| 46 | C₆H₅ | C₆H₅ | COCH₃ | H | 221–222.5 |
| 47 | 4-F-C₆H₄ | 4-F-C₆H₄ | COCH₂CF₃ | H | 207–209 |

TABLE 1-continued

Structure:
$$R^1\text{-C}(=\text{N-N}(A^1)(A^2))\text{-S-C}(R^2)=$$ (thiazoline-type with N-A¹, N-A², ring including S)

| Compound No. | R¹ | R² | A¹ | A² | Melting point (°C.) |
|---|---|---|---|---|---|
| 48 | phenyl | phenyl | COCH$_2$NH$_2$ | H | 204–206 (dec.) |
| 49 | CH$_3$ | phenyl | COCH$_2$NHCOOCH$_2$-phenyl | H | 167–168 |
| 50 | CH$_3$ | benzyl (C$_6$H$_5$CH$_2$) | SO$_2$CF$_3$ | H | 191–193 |
| 51 | phenyl | CH$_3$ | SO$_2$CF$_3$ | H | 96–97 |
| 52 | C$_6$H$_5$-CO-CH$_2$ | CH$_3$ | SO$_2$CF$_3$ | H | 97–99 |
| 53 | CH$_3$ | H | SO$_2$CF$_3$ | H | 218–221 |
| 54 | C$_6$H$_5$-CO- | CH$_3$ | SO$_2$CF$_3$ | SO$_2$CF$_3$ | 96–97 |
| 55 | 4-F-C$_6$H$_4$- | CH$_3$ | SO$_2$CF$_3$ | H | 130–132.5 |
| 56 | | H | SO$_2$CF$_3$ | H | 220–221 |

TABLE 1-continued

Structure:
$$R^1-C(=C(R^2)-S-)-N=C(-N(A^1)(A^2))$$
(thiazoline-type ring with N–A¹ and N–A² substituents)

| Compound No. | R¹ | R² | A¹ | A² | Melting point (°C.) |
|---|---|---|---|---|---|
| 57 | 2-thienyl | phenyl | SO₂CF₃ | H | 219–221 |
| 58 | phenyl | 2-benzoyl-phenyl | SO₂CF₃ | H | 217–219 |
| 59 | phenyl | 2-benzoyl-phenyl | SO₂CH₃ | H | 210–213 |
| 60 | CH₃ | CH₂COOC₂H₅ | SO₂CF₃ | SO₂CF₃ | 72–74 |
| 61 | CH₃ | 2-benzoyl-phenyl | SO₂CF₃ | H | 201–204 |
| 62 | CH₃ | 2-benzoyl-phenyl | SO₂CH₃ | H | 262–264 |
| 63 | 2-benzoyl-phenyl | phenyl | SO₂CH₃ | H | 210–215 |
| 64 | phenyl | cyclohexyl | SO₂CF₃ | H | 187–189 |
| 65 | phenyl | cyclohexyl | SO₂CH₃ | H | 205–207 |

TABLE 1-continued

Structure:

$$R^1-C(=C(R^2)-S-)-N=C-N(A^1)(A^2)$$
(cyclic thiazoline with R¹, R² on C=C, and N substituted with A¹, A² which may form ring)

| Compound No. | R¹ | R² | A¹ | A² | Melting point (°C.) |
|---|---|---|---|---|---|
| 66 | phenyl | cyclopentyl | SO₂CF₃ | H | 133–134 |
| 67 | phenyl | cyclopentyl | SO₂CH₃ | H | 205–207 |
| 68 | C₆H₅-CO- | CH₃ | SO₂CF₃ | H | 172–175 |
| 69 | 4-(CH₃S)-C₆H₄- | H | SO₂CF₃ | H | 182–184 |
| 70 | 4-(CH₃S)-C₆H₄- | i-Pr | SO₂CF₃ | H | 179–182 |
| 71 | 4-(CH₃S)-C₆H₄- | C₅H₁₁ | SO₂CF₃ | H | 120–122 |
| 72 | 4-(CH₃S)-C₆H₄- | CH₃ | 4-(OCF₃)-C₆H₄-SO₂- | H | 90–93 |
| 73 | 4-(CH₃S)-C₆H₄- | CH₃ | 4-(NO₂)-C₆H₄-SO₂- | H | 201–203 |

TABLE 1-continued

| Compound No. | R¹ | R² | A¹ | A² | Melting point (°C.) |
|---|---|---|---|---|---|
| 74 | 4-CH₃S-C₆H₄ | CH₃ | 4-NH₂-C₆H₄-SO₂ | H | 207–209 |
| 75 | 4-CH₃S-C₆H₄ | CH₃ | 4-OH-C₆H₄-CH₂ | H | 186–188 |
| 76 | 4-CH₃S-C₆H₄ | CH₃ | 4-N(CH₃)₂-C₆H₄-CH₂ | H | 126–128 |
| 77 | 4-CH₃S-C₆H₄ | CH₃ | 4-NHCOCH(CH₃)₂-C₆H₄-CO | H | 206–208 |
| 78 | 4-CH₃S-C₆H₄ | CH₃ | 4-NHCOCF₃-C₆H₄-CO | H | 239–240 |
| 79 | 4-HOCOCH₂-C₆H₄ | CH₃ | SO₂CF₃ | H | 273–275 |
| 80 | C₆H₅ | COOC₂H₅ | SO₂CF₃ | C₂H₅ | 164–165 |
| 81 | C₆H₅ | COOH | SO₂CF₃ | C₂H₅ | 245–250 |

TABLE 1-continued

| Compound No. | R¹ | R² | A¹ | A² | Melting point (°C.) |
|---|---|---|---|---|---|
| 82 | EtOCOCH₂-C₆H₄- | H | SO₂CF₃ | H | 168–170 |
| 83 | EtOCOCH₂O-C₆H₄- | H | SO₂CF₃ | H | 166–168 |
| 84 | HOCOCH₂- | phenyl | SO₂CF₃ | H | 169–172 |
| 85 | CH₃S-C₆H₄- | cyclopentyl | 4-(OCOt-Bu)-C₆H₄-SO₂- | H | 281–284 |
| 86 | CH₃S-C₆H₄- | CH₃ | 4-(OCOt-Bu)-C₆H₄-SO₂- | H | 176–178 |
| 87 | CH₃S-C₆H₄- | CH₃ | 4-(OCOt-Bu)-C₆H₄-SO₂- | H | 209–211 |
| 88 | CH₃S-C₆H₄- | CH₃ | 4-(OCOt-Bu)-C₆H₄-CO- | H | 184–185 |
| 89 | CH₃S-C₆H₄- | C₅H₁₁ | 3-(OCOt-Bu)-C₆H₄- | H | 70–72 |

TABLE 1-continued

| Compound No. | R¹ | R² | A¹ | A² | Melting point (°C.) |
|---|---|---|---|---|---|
| 90 | phenyl | phenyl | 4-(OCOt-Bu)-C₆H₄-CH₂ | H | 175–177 |
| 91 | phenyl | phenyl | 4-(OCOt-Bu)-C₆H₄-SO₂ | H | 237–239 |
| 92 | phenyl | 4-NO₂-C₆H₄ | 4-(OCOt-Bu)-C₆H₄-SO₂ | H | 203–205 |
| 93 | phenyl | C₂H₅OCO | 3-(OCOt-Bu)-C₆H₄ | H | 131–133 |
| 94 | phenyl | C₂H₅OCOCH₂ | 4-(OCOt-Bu)-C₆H₄-SO₂ | H | 166–168 |
| 95 | phenyl | HOCOCH₂ | 4-(OCOt-Bu)-C₆H₄-SO₂ | H | 207–210 |
| 96 | 4-CH₃-C₆H₄ | phenyl | 4-(OCOt-Bu)-C₆H₄-SO₂ | H | 251–253 |
| 97 | 4-CH₃O-C₆H₄ | CH₂OCOCH₂-phenyl | 4-(OCOt-Bu)-C₆H₄-SO₂ | H | 137–140 |

TABLE 1-continued

Structure: R¹ and R² on C=C, with C bonded to S and to C(=N...)-N(A¹)(A²) forming a ring

| Compound No. | R¹ | R² | A¹ | A² | Melting point (°C.) |
|---|---|---|---|---|---|
| 98 | 4-CH₃O-C₆H₄- | 4-Cl-C₆H₄- | 4-(t-BuOCO)-C₆H₄-SO₂- | H | 268–269 |
| 99 | 4-CH₃O-C₆H₄- | cyclohexyl | 4-(t-BuOCO)-C₆H₄-SO₂- | H | 233–236 |
| 100 | CH₃ | C₆H₅-CH₂- | 4-(t-BuOCO)-C₆H₄-SO₂- | H | 237–238 |
| 101 | C₆H₅-CO- | CH₃ | 4-(t-BuOCO)-C₆H₄-SO₂- | H | 186–188 |
| 102 | C₆H₅-COCH₂- | H | 4-(t-BuOCO)-C₆H₄-SO₂- | H | 241–243 |
| 103 | 4-(t-BuCOO)-C₆H₄- | CH₃ | 4-(t-BuOCO)-C₆H₄-SO₂- | H | 215–217 |
| 104 | 4-(t-BuCOO)-C₆H₄- | CH₃ | 2-CH₃O-C₆H₄- | H | 112–114 |

TABLE 1-continued

Structure: R¹, R² on C=C, with C=S bearing N(A¹)(A²) (A¹ and A² may form a ring)

| Compound No. | R¹ | R² | A¹ | A² | Melting point (°C.) |
|---|---|---|---|---|---|
| 105 | 4-(t-BuCOO)C₆H₄– | CH₃ | –(CH₂)₃–N(morpholine ring closure with A²) | H | 125–126 |
| 106 | 4-(t-BuCOO)C₆H₄– | C₆H₅ | SO₂CF₃ | H | 210–212 |
| 107 | 4-(t-BuCOO)C₆H₄– | C₆H₅ | SO₂C₆H₅ | H | 222–223 |
| 108 | 4-(t-BuCOO)C₆H₄– | CH₃ | COCH₂CH₂COOH | H | 222–223 |
| 109 | 4-(t-BuCOO)C₆H₄– | CH₃ | COCH₂NHCOOCH₂C₆H₅ | H | 207–209 |
| 110 | 4-(t-BuCOO)C₆H₄– | H | COCH₂CH₂COOH | H | 268–270 |
| 111 | 4-(t-BuCOO)C₆H₄– | CH₃ | CH(CH₃)CH₂CH(CH₃) | H | 138–140 |
| 112 | 4-(t-BuCOO)C₆H₄– | CH₃ | cyclohexyl | H | 120–122 |

TABLE 1-continued

| Compound No. | R¹ | R² | A¹ | A² | Melting point (°C.) |
|---|---|---|---|---|---|
| 113 | 4-(t-BuCOO)-C₆H₄- | CH₃ | 4-HO-C₆H₄-CH₂- | H | 128–129 |
| 114 | 4-(t-BuCOO)-C₆H₄- | CH₃ | 4-(N(CH₃)₂)-C₆H₄-CH₂- | H | 124–126 |
| 115 | 4-(t-BuCOO)-C₆H₄- | CH₃ | CH₃-C(NH₂)=NH | H | 163–165 |
| 116 | 4-(t-BuCOO)-C₆H₄- | CH₃ | 3-CF₃-C₆H₄-CH₂- | H | 154–157 |
| 117 | 4-(t-BuCOO)-C₆H₄- | CH₃ | 6-CH₃-pyridin-2-yl | H | 175–177 |
| 118 | 4-(t-BuCOO)-C₆H₄- | CH₃ | 4,6-(CH₃)₂-pyridin-2-yl | H | 185–187 |
| 119 | 4-(t-BuCOO)-C₆H₄- | CH₃ | pyridin-2-yl-CH₂- | H | 138–139 |

TABLE 1-continued

| Compound No. | R¹ | R² | A¹ | A² | Melting point (°C.) |
|---|---|---|---|---|---|
| 120 | 4-(t-BuCOO)C₆H₄ | CH₃ | morpholino (via (CH₂)₂·N·O) | H | 127–129 |
| 121 | 4-(t-BuCOO)C₆H₄ | CH₃ | (CH₂)₄·N·O | H | 115–117 |
| 122 | 4-(t-BuCOO)C₆H₄ | CH₃ | SO₂CF₃ | H | 189–190 |
| 123 | 4-(t-BuCOO)C₆H₄ | CH₃ | SO₂CH₂CF₃ | H | 182–183 |
| 124 | 4-(t-BuCOO)C₆H₄ | CH₃ | SO₂CH₂Cl | H | 164–165 |
| 125 | 4-(t-BuCOO)C₆H₄ | CH₃ | 4-Cl-C₆H₄-SO₂ | H | 222–224 |
| 126 | 4-(t-BuCOO)C₆H₄ | CH₃ | 4-NO₂-C₆H₄-SO₂ | H | 107–109 |
| 127 | 4-(t-BuCOO)C₆H₄ | CH₃ | 4-(OCOt-Bu)-C₆H₄-SO₂ | H | 215–217 |

TABLE 1-continued $$\underset{R^2}{\overset{R^1}{\diagdown}}C=C\overset{N}{\underset{S}{\diagdown}}C-N\overset{A^1}{\underset{A^2}{\diagdown}}$$

| Compound No. | R¹ | R² | A¹ | A² | Melting point (°C.) |
|---|---|---|---|---|---|
| 128 | 4-(t-BuCOO)C₆H₄ | CH₃ | NHCOCH₃ | H | 227–229 |
| 129 | 4-(t-BuCOO)C₆H₄ | CH₃ | COC₆H₅ | H | 146–147 |
| 130 | 4-(t-BuCOO)C₆H₄ | CH₃ | 4-[NHCOCH(CH₃)₂]C₆H₄CO | H | 270–272 |
| 131 | 4-(t-BuCOO)C₆H₄ | CH₃ | CO(CH₂)₃COOH | H | 244–245 |
| 132 | 4-(t-BuCOO)C₆H₄ | CH₃ | 2-(HOOC)C₆H₄CO | H | 185–186 |
| 133 | 4-(t-BuCOO)C₆H₄ | CH₃ | COCH₂NHCOOt-Bu | H | 212–215 |
| 134 | 4-(t-BuCOO)C₆H₄ | CH₃ | succinimido (A¹–N–A² = succinimide) | | 182–183 |

TABLE 1-continued

| Compound No. | R¹ | R² | A¹ | A² | Melting point (°C.) |
|---|---|---|---|---|---|
| 135 | 4-(t-BuCOO)C₆H₄ | C₆H₅ | H | H | 180–182 |
| 136 | 4-(t-BuCOO)C₆H₄ | C₆H₅ | CH₃ | H | 202–203 |
| 137 | 4-(t-BuCOO)C₆H₄ | C₆H₅ | SO₂CH₃ | H | 195–203 |
| 138 | 4-(t-BuCOO)C₆H₄ | C₆H₅ | (CH₂)₃OCH(CH₃)CH₃ | H | 117–119 |
| 139 | 4-(t-BuCOO)C₆H₄ | C₆H₅ | CO(CH₂)₂COOH | H | 228–230 |
| 140 | 4-(t-BuCOO)C₆H₄ | C₆H₅ | CO(CH₂)₂COOH | H | 237–239 |
| 141 | 4-(t-BuCOO)C₆H₄ | C₆H₅ | 2-(HOOC)C₆H₄CO | H | 191–193 |
| 142 | 4-(t-BuCOO)C₆H₄ | 4-Cl-C₆H₄ | C₆H₅CH₂CH₂ | H | 213–214 |

TABLE 1-continued
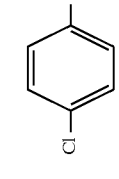
| Compound No. | R¹ | R² | A¹ | A² | Melting point (°C.) |
|---|---|---|---|---|---|
| 143 | 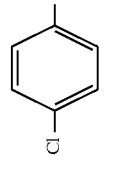 t-BuCOO | 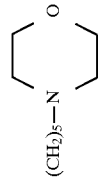 Cl | 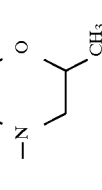 (CH₂)₅—N | H | 156–157 |
| 144 | 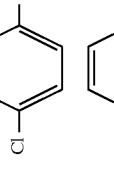 t-BuCOO | 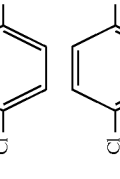 Cl | 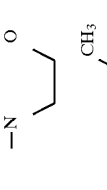 | — | 150–152 |
| 145 |  t-BuCOO | 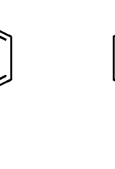 Cl | 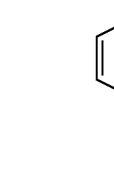 | — | 177–179 |
| 146 | 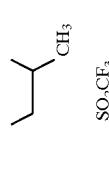 t-BuCOO |  Cl | $SO_2CF_3$ | H | 205–207 |
| 147 | 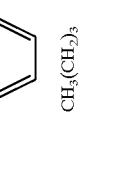 t-BuCOO | $CH_3(CH_2)_3$ | $CO(CH_2)_2COOH$ | H | 187–189 |
| 148 | 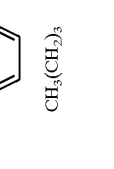 t-BuCOO | $CH_3(CH_2)_4$ | $CO(CH_2)_2COOH$ | H | 195–197 |
| 149 |  t-BuCOO | $CH_3(CH_2)_5$ | $CO(CH_2)_2COOH$ | H | 175–177 |

TABLE 1-continued

| Compound No. | R¹ | R² | A¹ | A² | Melting point (°C.) |
|---|---|---|---|---|---|
| 150 | 4-(t-BuCOO)-C₆H₄ | CH₃(CH₂)₇ | CO(CH₂)₂COOH | H | 172–174 |
| 151 | 4-(t-BuCOO)-C₆H₄ | (CH₃)₂CH | CO(CH₂)₂COOH | H | 204–205 |
| 152 | 4-(t-BuCOO)-C₆H₄ | (CH₃)₂CH | 2-HOOC-C₆H₄-CO | H | 180–182 |
| 153 | 4-(t-BuCOO)-C₆H₄ | CH₂C₆H₅ | CO(CH₂)₂COOH | H | 218–220 |
| 154 | 4-(t-BuCOO)-C₆H₄ | CH₂C₆H₅ | 2-HOOC-C₆H₄-CO | H | 163–164 |
| 155 | 4-(t-BuCOO)-C₆H₄ | HOCOCH₂ | CH₃ | H | 219–221 |
| 156 | 4-(t-BuCOO)-C₆H₄ | HOCOCH₂ | (CH₂)₃-morpholino | H | 195–198 |

TABLE 1-continued

| Compound No. | R¹ | R² | A¹ | A² | Melting point (°C.) |
|---|---|---|---|---|---|
| 157 | 4-(t-BuCOO)C₆H₄ | HOCOCH₂ | SO₂CF₃ | H | 193–195 |
| 158 | 4-(t-BuCOO)C₆H₄ | Cl | H | H | 160–162 |
| 159 | 4-(t-BuCOO)C₆H₄ | 4-NO₂-C₆H₄-CH₂OCOCH₂ | H | H | 157–158 |
| 160 | 4-(t-BuCOO)C₆H₄ | 4-NO₂-C₆H₄-CH₂OCOCH₂ | CH₃ | H | 70–73 |
| 161 | 4-(t-BuCOO)C₆H₄ | 4-(t-BuCOO)C₆H₄ | SO₂CF₃ | H | 207–208 |
| 162 | C₆H₅ | 4-(t-BuCOO)C₆H₄ | SO₂CF₃ | H | 230–233 |
| 163 | C₆H₅ | 4-(t-BuCOO)C₆H₄ | SO₂C₆H₅ | H | 237–239 |
| 164 | 4-HO-C₆H₄ | 4-HO-C₆H₄ | SO₂CF₃ | H | 258.4–260.8 (3/2H₂O salt) |

TABLE 1-continued

Structure:
R¹-C(=C(R²)-S-)-N(A¹)(A²) (cyclic with dashed bond between A¹ and A²)

| Compound No. | R¹ | R² | A¹ | A² | Melting point (°C.) |
|---|---|---|---|---|---|
| 165 | 4-CH₃O-C₆H₄- | 4-Cl-C₆H₄- | 4-OH-C₆H₃(SO₂-)- (phenol with SO₂ linker) | H | 139–144 |
| 166 | 4-HO-C₆H₄- | C₆H₅- | 2-HOOC-C₆H₄-CO- | H | 189–190 |
| 167 | 4-HO-C₆H₄- | C₆H₅- | -CO(CH₂)₂COOH | H | 231–232 |
| 168 | 4-HO-C₆H₄- | -CH(CH₃)₂ | 2-HOOC-C₆H₄-CO- | H | 172–173 |
| 169 | 4-HO-C₆H₄- | CH₃ | -C(=NH)NH₂ | H | 245–250 (dec.) (HCl salt) |
| 170 | 4-HO-C₆H₄- | CH₃ | C₆H₅-CO- | H | 257–259 |
| 171 | 4-HO-C₆H₄- | CH₃ | -(CH₂)₃-N(morpholino) | H | 215–225 (dec.) |

TABLE 1-continued
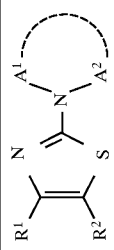
| Compound No. | R$^1$ | R$^2$ | A$^1$ | A$^2$ | Melting point (°C.) |
|---|---|---|---|---|---|
| 172 | 4-HO-C$_6$H$_4$ | CH$_3$ | 2-HOOC-CO-C$_6$H$_4$ | H | 195–197 |
| 173 | C$_6$H$_5$ | C$_6$H$_5$ | 4-(4-OCOt-Bu-C$_6$H$_4$-NHSO$_2$)-C$_6$H$_4$-SO$_2$ | H | 209–211 |

Formulation examples for preparations using the 2-aminothiazole derivative having antibacterial or bactericidal activity according to this invention will be described.

The compound represented by the general formula (I) may be administered as such or in combination with a conventional carrier for preparations. The administration unit form is not particularly limited and may be suitably selected according to need. It should be noted that the following formulation examples are merely given by way of example and various formulations for preparations may be possible according to conventional methods.

PREPARATION FORMULATION EXAMPLE 1

A cream is prepared according to the following formulation (total amount: 100 parts by weight).

| | |
|---|---|
| Compound represented by the general formula (I) | 2 |
| Diisopropyl adipate | 5 |
| Pirotiodecane | 3 |
| Polyoxyethylene (23) sorbitan | 5 |
| Stearyl alcohol | 5 |
| Cetanol | 5 |
| Octyldodecanol | 5 |
| White petrolatum | 10 |
| Macrogol 400 | 10 |
| Methylparaben | 0.2 |
| Purified water | Balance |
| | 100 |

PREPARATION FORMULATION EXAMPLE 2

An ointment is prepared according to the following formulation (total amount: 100 parts by weight).

| | |
|---|---|
| Compound represented by the general formula (I) | 2 |
| Diisopropyl adipate | 5 |
| Pirotiodecane | 3 |
| Macrogol 400 | 10 |
| Sorbitan monostearate | 5 |
| Octyldodecanol | 20 |
| Microcrystalline wax | 10 |
| White petrolatum | Balance |
| | 100 |

PREPARATION FORMULATION EXAMPLE 3

A lotion is prepared according to the following formulation (total amount: 100 parts by weight).

| | |
|---|---|
| Compound represented by the general formula (I) | 2 |
| Diisopropyl adipate | 5 |
| Macrogol 400 | 10 |
| Oleyl alcohol | 5 |
| Ethanol | 50 |
| Purified water | Balance |
| | 100 |

PREPARATION FORMULATION EXAMPLE 4

A gel is prepared according to the following formulation (total amount: 100 parts by weight).

| | |
|---|---|
| Compound represented by the general formula (I) | 2 |
| Diisopropyl adipate | 5 |
| Pirotiodecane | 3 |
| Propylene glycol | 10 |
| Macrogol 400 | 10 |
| Polyoxyethylene (60) hydrogenated castor oil | 1 |
| Ethanol | 40 |
| Carbopol 940 | 3 |
| Hydroxypropyl cellulose | 1 |
| Diisopropanolamine | 1.5 |
| Purified water | Balance |
| | 100 |

PREPARATION FORMULATION EXAMPLE 5

An injection (0.1%) is prepared according to the following formulation.

| | |
|---|---|
| Compound represented by the general formula (I) | 5 mg |
| Tromethamine | 30 mg |
| Physiological saline | 5 ml |
| Aqueous injection pH 9.5 | |

PREPARATION FORMULATION EXAMPLE 6

An injection (0.1%) is prepared according to the following formulation.

| | |
|---|---|
| Compound represented by the general formula (I) | 5 mg |
| Tromethamine | 20 mg |
| α-Cyclodextrin | 50 mg |
| Physiological saline | 5 ml |
| Aqueous injection pH 9.25 | |

PREPARATION FORMULATION EXAMPLE 7

An injection (0.1%) is prepared according to the following formulation.

| | |
|---|---|
| Compound represented by the general formula (I) | 5 mg |
| Tromethamine | 5 mg |
| 2-Hydroxypropyl-β-cyclodextrin | 50 mg |
| Physiological saline | 5 ml |
| Aqueous injection pH 8.5 | |

PREPARATION FORMULATION EXAMPLE 8

An injection (0.1%) is prepared according to the following formulation.

| | |
|---|---|
| Compound represented by the general formula (I) | 5 mg |
| Tromethamine | 5 mg |
| Polyoxyethylene sorbitan monooleate | 50 mg |

| | |
|---|---|
| Physiological saline | 5 ml |
| Aqueous injection pH 8.6 | |

PREPARATION FORMULATION EXAMPLE 9

A liquid preparation was prepared by a conventional method using 0.5 g of a compound represented by the general formula (I), 65 g of ethanol, 1 g of polyoxyethylene lauryl ether (HLB 11.5), 3 g of glycerin, a dimethylsiloxane/methyl(POE)siloxane copolymer (HLB 13.0), 10 g of a 0.5% aqueous xanthane gum solution (0.05 g as xanthane gum) and 19.5% of water. This liquid preparation may be used as disinfectants.

The pharmacological activity of the compounds represented by the formula (I) will be described.

The antibacterial activity or bactericidal activity of various compounds represented by the formula (I) was evaluated by the following experiment examples.

EXPERIMENT EXAMPLE 1

Antibacterial Activity Against Gram-positive Bacteria (1) Preparation of Bacteria Suspension One platinum loop (oese) of a test strain on a slant culture medium was inoculated into 10 ml of each growing medium (for aerobic bacteria: Trypto-Soya Broth manufactured by Nussui Pharmaceutical Co., Ltd., for anaerobic bacteria: GAM Broth manufactured by Nussui Pharmaceutical Co., Ltd.) and cultured at. 37° C. for 18 to 20 hr. The cultures thus obtained were each diluted to obtain suspensions of about $10^7$ cells/ml which were later used as a bacteria suspension for inoculation.

(2) Sample Solution

About 10 mg of each sample were weighed out and dissolved in such an amount of DMSO (dimethylsulfoxide) as to obtain sample solutions having a concentration of 10 mg/ml.

(3) Sample-Containing Liquid Medium

The sample solutions thus prepared were each added to each liquid medium (for aerobic bacteria: broth for determination of sensitivity, manufactured by Nussui Pharmaceutical Co., Ltd., for anaerobic bacteria: GAM Broth manufactured by Nussui Pharmaceutical Co., Ltd.) to obtain sample-containing medium solutions having a concentration of 128 µg/ml. Further, the thus obtained solutions were each subjected to progressive or stepwise two-fold dilutions on a microplate with wells each containing 100 ml of the above medium (until various concentrations in a range from 128 down to 0.063 µg/ml were obtained).

(4) Inoculation of Bacteria, Culture and Judgment 5 ml of each bacteria suspension for inoculation were placed in each of the sample-containing liquid media so prepared, and the bacteria were cultured at 37° C. for 18 to 20 hr. Thereafter, the growth of bacteria was observed. The minimum concentrations of the samples, which have been judged to completely inhibit the growth of bacteria, are expressed as MIC (Minimum Inhibitory Concentration) in µg/ml.

The results on the antibacterial activity of the samples against *Staphylococcus aureus:* IFO 13276 are given in Table 2, and the results on the antibacterial activity of the samples against various Gram-positive bacteria (*Staphylococcus epidermidis:* IFO 12993, *Streptococcus agalactiae:* IID 1624, *Streptococcus pyogenes:* IID 698, *Bacillus subtilis:* IFO 3134, and *Propionibacterium acnes:* Clinical isolated No. 3) are summarized in Tables 3 to 5. The results on the antibacterial activity of Gentamicin sulfate (GM) as a control pharmaceutical are also shown in the tables.

TABLE 2

| Compound NO. | MIC (µg/ml) |
|---|---|
| 1 | 8 |
| 2 | 16 |
| 3 | 16 |
| 4 | 32 |
| 6 | 4 |
| 7 | 16 |
| 8 | 8 |
| 9 | 8 |
| 10 | 8 |
| 11 | 8 |
| 12 | 4 |
| 13 | 8 |
| 14 | 16 |
| 15 | 8 |
| 16 | 32 |
| 17 | 128 |
| 18 | 128 |
| 19 | 128 |
| 23 | 128 |
| 25 | 64 |
| 27 | 4 |
| 28 | 8 |
| 29 | 8 |
| 30 | 8 |
| 31 | 8 |
| 32 | 64 |
| 33 | 8 |
| 34 | 16 |
| 36 | 8 |
| 28 | 16 |
| 40 | 8 |
| 41 | 128 |
| 42 | 128 |
| 43 | 16 |
| 44 | 8 |
| 47 | 16 |
| 48 | 64 |
| 50 | 32 |
| 51 | 128 |
| 52 | 64 |
| 57 | 16 |
| 64 | 16 |
| 66 | 8 |
| 69 | 64 |
| 70 | 8 |
| 71 | 4 |
| 72 | 8 |
| 82 | 128 |
| 85 | 128 |
| 91 | 2 |
| 94 | 64 |
| 98 | 2 |
| 106 | 8 |
| 107 | 4 |
| 115 | 16 |
| 124 | 64 |
| 141 | 32 |
| 146 | 4 |
| 149 | 16 |
| 150 | 8 |
| 152 | 128 |
| 154 | 16 |
| 161 | 4 |
| 162 | 8 |
| 163 | 2 |
| 173 | 2 |
| GM | 2 |

TABLE 3

| | MIC (μg/ml) Compound No. | | | | |
|---|---|---|---|---|---|
| | 6 | 8 | 9 | 10 | 12 |
| Staphylococcus epidermidis | 2 | 4 | 8 | 4 | 2 |
| Streptococcus agalactiae | 2 | 4 | 8 | 2 | 1 |
| Streptococcus pyogenes | 4 | 4 | 8 | 4 | 1 |
| Bacillus subtilis | 2 | 4 | 8 | 4 | 1 |
| Propionibacterium acnes | 4 | 2 | 4 | 4 | 2 |

TABLE 4

| MIC (μg/ml) Compound No. | | | | | | | |
|---|---|---|---|---|---|---|---|
| 27 | 28 | 29 | 30 | 66 | 70 | 71 | 72 |
| 4 | 4 | 4 | 2 | 8 | 16 | 2 | 8 |
| 2 | 4 | 4 | 2 | 8 | 8 | 1 | 8 |
| 4 | 8 | 4 | 4 | 16 | 8 | 2 | 8 |
| 2 | 4 | 4 | 2 | 8 | 8 | 1 | 8 |
| 8 | 4 | 2 | 2 | 4 | 4 | 2 | >128 |

TABLE 5

| MIC (μg/ml) Compound No. | | | | | | |
|---|---|---|---|---|---|---|
| 85 | 91 | 98 | 107 | 161 | 163 | GM |
| 4 | 2 | 2 | 4 | 2 | 4 | 0.5 |
| 2 | 2 | 2 | 2 | 2 | 2 | 16 |
| >128 | 4 | 2 | 4 | 2 | 4 | 2 |
| 4 | 2 | 4 | 2 | 2 | 4 | 0.25 |
| >128 | >128 | 128 | 16 | 4 | 4 | 32 |

EXPERIMENT EXAMPLE 2

Acquisition of Tolerance in *Staphylococcus aureus* and *Staphylococcus epidermidis*

(1) Preparation of Bacteria Suspension

One platinum loop of each test strain on a slant culture medium was inoculated into 10 ml of a growing medium (Trypto-Soya Broth manufactured by Nussui Pharmaceutical Co., Ltd.) and cultured at 37° C. for 18 to 20 hr. The thus obtained cultures were each diluted to obtain suspensions of about $10^8$ cells/ml which were later used as a bacteria suspension for inoculation.

(2) Sample Solution

About 10 mg of compound No. 9 were weighed out and dissolved in such an amount of DMSO as to obtain a solution having a concentration of 12.8 mg/ml, after which the solution so obtained was subjected to stepwise two-fold dilutions with DMSO (12.8 to 0.1 mg/ml).

Separately, about 400 mg of Gentamicin sulfate (GM) were weighed and dissolved in distilled water to obtain a solution having a concentration of 409.6 mg/ml, after which the solution so obtained was subjected to stepwise two-fold dilutions with distilled water to prepare control medicinal solutions for comparison (409.6 to 0.1 mg/ml).

(3) Sample-Containing Liquid Medium

Each of the sample solutions thus obtained by the stepwise dilutions was added to a liquid medium (Trypto-Soya Broth manufactured by Nussui Pharmaceutical Co., Ltd.) in an amount of 0.01 volume thereof.

(4) Inoculation of Bacteria, Culture and Judgment

Each of the bacteria suspensions for inoculation was added to each of the sample-containing liquid media so prepared in an amount of 0.01. volume (about $10^6$ cells/ml) of the liquid medium, and the bacteria were cultured at 37° C. for 2 to 4 days. Thereafter, the growth of bacteria was observed. The minimum concentrations of compound No. 9 and GM, which have been judged to completely inhibit the growth of bacteria, are expressed as MIC (Minimum Inhibitory Concentration) in μg/ml. Further, bacteria suspensions of ½ MIC were each added in an amount of 0.01 volume to a fresh sample-containing medium, followed by 10 to 18 passages in this way.

The results of the test on the acquisition of tolerance of *Staphylococcus aureus* are shown in FIG. 1. As a result, compound No. 9 did not induce bacterial tolerance until 10 passages. On the other hand, GM highly induced the tolerance.

Figure 2:
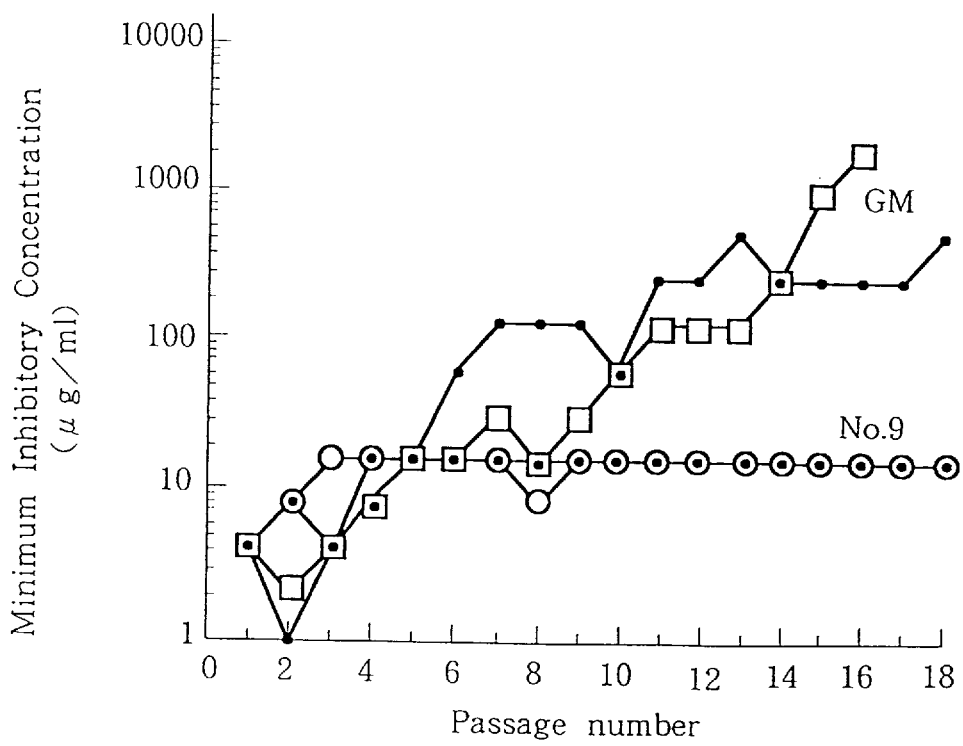
* and FIG. 2 is graphs showing the relationship between the Minimum Inhibitory Concentration (MIC) and the passage number for *Staphylococcus epidermidis.*

The results of the test on the acquisition of tolerance of *Staphylococcus epidermidis* are shown in FIG. 2. As a result, compound No. 9 did not induce the tolerance until 18 passages. On the other hand, GM highly induced the tolerance.

EXPERIMENT EXAMPLE 3

Antibacterial Activity Against GM-Sensitive and Tolerant Strains of *Staphylococcus aureus* and *Staphylococcus epidermidis*

(1) Preparation of Bacteria Suspension

One platinum loop of each test strain on a slant culture medium was inoculated into 10 ml of a growing medium (Trypto-Soya Broth manufactured by Nussui Pharmaceutical Co., Ltd.) and cultured at 37° C. for 18 to 20 hr. The thus obtained cultures were each diluted to obtain suspensions of about $10^7$ cells/ml which were later used as a bacteria suspension for inoculation.

(2) Sample Solution

About 10 mg of compound No. 9 were weighed out and dissolved in such an amount of DMSO as to obtain a solution having a concentration of 10 mg/ml. Separately, about 400 mg of Gentamicin sulfate (GM) were weighed out and dissolved in distilled water to obtain a solution having a concentration of 409.6 mg/ml.

(3) Sample-Containing Liquid Medium

Each of the sample solutions thus prepared was added to a liquid medium (broth for determination of sensitivity, manufactured by Nussui Pharmaceutical Co., Ltd.) to obtain a liquid medium containing compound No. 9 in a concentration of 128 μg/ml or GM in a concentration of 4096 μg/ml. Further, each sample-containing medium so obtained was subjected to stepwise two-fold dilutions on a microplate with wells each containing 100 ml of the above medium (compound No. 9: 128 to 1 μg/ml, GM: 4096 to 1 μg/ml).

(4) Inoculation of Bacteria, Culture and Judgement 5 ml of each bacteria suspension for inoculation were placed in each of the sample-containing liquid media so prepared, and the bacteria were cultured at 37° C., for 4 days. Thereafter, the growth of bacteria was observed. The minimum concentrations of the samples, which have been judged to completely inhibit the growth of bacteria, are expressed as MIC (Minimum Inhibitory Concentration) in μg/ml.

The results are given in Table 6.

TABLE 6

| | MIC (µg/ml) | |
|---|---|---|
| | Compound No. 9 | GM |
| *Staphylococcus aureus* | | |
| sensitive to GM | 8 | 2 |
| tolerant to GM | 8 | 2048 |
| *Staphylococcus epidermidis* | | |
| sensitive to GM | 8 | 0.5 |
| tolerant to GM | 8 | 1024 |

EXPERIMENT EXAMPLE 4

Antibacterial Activity Against Gram-Negative Bacteria

The procedure was performed in the same manner as Experiment Example 1.

The results on the antibacterial activity against *Escherichia coli*: IFO 3972, are given in Table 7. The results on that of Gentamicin sulfate (GM) as a control pharmaceutical are also shown in the table.

TABLE 7

| Compound No. | MIC (µg/ml) |
|---|---|
| 103 | 128 |
| 169 | 128 |
| GM | 2 |

EXPERIMENT EXAMPLE 5

Bactericidal Activity Against Gram-Positive Bacteria (1) Preparation of Bacteria Suspension One platinum loop of each test strain on a slant culture medium was inoculated into 10 ml of each growing medium (for aerobic bacteria: Trypto-Soya Broth manufactured by Nussui Pharmaceutical Co., Ltd., for anaerobic bacteria: GAM Broth manufactured by Nussui Pharmaceutical Co., Ltd.) and cultured at 37° C. for 18 to 20 hr. The thus obtained cultures were each diluted to obtain suspensions of about $10^7$ cells/ml which were later used as a bacteria suspension for inoculation.

(2) Sample Solution

About 10 mg of each sample were weighed out and dissolved in such an amount of DMSO (dimethylsulfoxide) as to obtain solutions having a concentration of 10 mg/ml.

(3) Sample-Containing Liquid Medium

The sample solutions thus prepared were each added to each liquid medium (for aerobic bacteria: broth for determination of sensitivity, manufactured by Nussui Pharmaceutical Co., Ltd., for anaerobic bacteria: GAM Broth manufactured by Nussui Pharmaceutical Co., Ltd.) to obtain sample-containing medium solutions having a concentration of 128 µg/ml. Further, the solutions so obtained were each subjected to stepwise two-fold dilutions on a microplate with wells each containing 100 ml of the above medium (128 to 0.063 µg/ml).

(4) Inoculation of Bacteria, Culture and Judgement

5 µl of each bacteria suspension for inoculation were placed in each of the sample-containing liquid media so prepared, and the bacteria were cultured at 37° C. for 18 to 20 hr. Thereafter, the growth of bacteria was observed. The minimum concentrations of the samples, which have been judged to kill bacteria, are expressed as MCC (Minimum Cidal Concentration) in µg/ml.

The results on the bactericidal activity against *Staphylococcus aureus*: IFO 13276 are given in Table 8, and the results on the bactericidal activity against various Gram-positive bacteria (*Staphylococcus epidermidis*: IFO 12993 and *Propionibacterium acnes*: Clinical isolated No. 3) are summarized in Table 9. The results on that of Gentamicin sulfate (GM) as a control pharmaceutical are also shown in the tables.

TABLE 8

| Compound No. | MIC (µg/ml) |
|---|---|
| 1 | 128 |
| 2 | 128 |
| 3 | 32 |
| 4 | 128 |
| 7 | 16 |
| 8 | 4 |
| 9 | 32 |
| 10 | 8 |
| 11 | 8 |
| 12 | 4 |
| 13 | 32 |
| 15 | 16 |
| 16 | 128 |
| 17 | 128 |
| 27 | 128 |
| 28 | 16 |
| 29 | 16 |
| 30 | 8 |
| 31 | 32 |
| 32 | 64 |
| 33 | 32 |
| 34 | 64 |
| 36 | 32 |
| 37 | 16 |
| 38 | 32 |
| 40 | 8 |
| 44 | 64 |
| 48 | 128 |
| 52 | 128 |
| 57 | 32 |
| 64 | 16 |
| 66 | 64 |
| 70 | 64 |
| 71 | 4 |
| 106 | 32 |
| 115 | 128 |
| 141 | 8 |
| 146 | 64 |
| 150 | 64 |
| 152 | 128 |
| 154 | 16 |
| 161 | 2 |
| 162 | 8 |
| 163 | 32 |
| GM | 128 |

TABLE 9

| | MIC (µg/ml) | |
|---|---|---|
| | Compound No. 9 | GM |
| *Staphylococcus epidermidis* | 64 | 64 |
| *Propionibacterium acnes* | 16 | 64 |

Thus, it has been found that the 2-aminothiazole derivatives according to this invention have antibacterial or bactericidal activity against aerobic and anaerobic various Gram-positive bacteria and Gram-negative bacteria. 10 and 18 passages respectively of *Staphylococcus aureus* and *Staphylococcus epidermidis* in a medium containing Gentamicin sulfate (GM) resulted in an increase in MIC (Minimum Inhibitory Concentration) to about 1000 µg/ml, indicating that these strains acquired their tolerance to Gentamicin sulfate (GM). By contrast, neither of the strains caused a significant increase in MIC (Minimum Inhibitory concentration) due to passages and induced its tolerance to compound No. 9. This suggests the compounds represented by the general formula (I) have mycological safety. Further, compound No. 9 exhibited antibacterial activity and bactericidal activity against the *Staphylococcus aureus* and *Staphylococcus epidermidis* each tolerant to Gentamicin sulfate (GM), said activities being equally powerful to those against the strains sensitive to Gentamicin sulfate (GM). This suggests that the compounds represented by the general formula (I) have a possibility that they have stable activity even against bacteria having tolerance to multiple antibacterial agents.

INDUSTRIAL APPLICABILITY

As is apparent from the above description, the antibacterial agent or bactericide of this invention, comprising a 2-aminothiazole derivative or a salt thereof is a promising pharmaceutical effective for infectious diseases induced by bacteria, for example, pyoderma, eczema, acne and decubitus, and, in addition, erosion, skin ulcer and secondary infection derived from other diseases.

We claim:

1. A method of treating a bacterial infection in a mammal in need thereof comprising administering to said mammal an antibacterial effective amount or a bactericide effective amount of a member selected from the group consisting of a 2-aminothiazole derivative represented by the following formula (I) and a salt thereof:

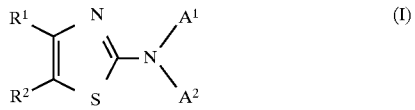

wherein
    $R^1$ and $R^2$ are each independently a substituted or unsubstituted phenyl group; and
    $A^1$ and $A^2$ are each independently a hydrogen atom, a lower alkanesulfonyl group or a halo lower alkanesulfonyl group.

2. The method of treating a bacterial infection as recited in claim 1, wherein in the 2-aminothiazole derivative of formula (I), $R^1$ is p-methoxyphenyl, $R^2$ is phenyl, $A^1$ is $SO_2CF_3$ and $A^2$ is H.

3. The method of treating a bacterial infection recited in claim 1, wherein said bacterial infection is induced by Gram-positive bacteria.

4. The method of treating a bacterial infection as recited in claim 3, wherein in the 2-aminothiazole derivative of formula (I), $R^1$ is p-methoxyphenyl, $R^2$ is phenyl, $A^1$ is $SO_2CF_3$ and $A^2$ is H.

5. The method of treating a bacterial infection recited in claim 1, wherein said antibacterial effective amount or a bactericide effective amount of said 2-aminothiazole derivative is administered by injection.

6. The method of treating a bacterial infection as recited in claim 5, wherein in the 2-aminothiazole derivative of formula (I), $R^1$ is p-methoxyphenyl, $R^2$ is phenyl, $A^1$ is $SO_2CF_3$ and $A^2$ is H.

7. The method of treating a bacterial infection recited in claim 1, wherein said antibacterial effective amount or a bactericide effective amount of said 2-aminothiazole derivative is administered locally.

8. The method of treating a bacterial infection as recited in claim 7, wherein in the 2-aminothiazole derivative of formula (I), $R^1$ is p-methoxyphenyl, $R^2$ is phenyl, $A^1$ is $SO_2CF_3$ and $A^2$ is H.

9. The method of treating a bacterial infection recited in claim 1, wherein said antibacterial effective amount or a bactericide effective amount of said 2-aminothiazole derivative is administered orally.

10. The method of treating a bacterial infection as recited in claim 9, wherein in the 2-aminothiazole derivative of formula (I), $R^1$ is p-methoxyphenyl, $R^2$ is phenyl, $A^1$ is $SO_2CF_3$ and $A^2$ is H.

* * * * *